US008880276B2

(12) United States Patent
Qiao et al.

(10) Patent No.: US 8,880,276 B2
(45) Date of Patent: Nov. 4, 2014

(54) ENGINE FRICTION BASED OIL VISCOSITY MONITOR

(75) Inventors: Ningsheng Qiao, Troy, MI (US); Kevin Joseph Bush, Northville, MI (US)

(73) Assignee: Continental Automotive Systems, Inc., Auburn Hills, MI (US)

( * ) Notice: Subject to any disclaimer, the term of this patent is extended or adjusted under 35 U.S.C. 154(b) by 140 days.

(21) Appl. No.: 13/482,657

(22) Filed: May 29, 2012

(65) Prior Publication Data

US 2012/0303230 A1 Nov. 29, 2012

Related U.S. Application Data

(60) Provisional application No. 61/490,340, filed on May 26, 2011.

(51) Int. Cl.
  *G01M 17/00* (2006.01)
  *G01N 33/18* (2006.01)
(52) U.S. Cl.
  CPC ............ *G01N 33/1826* (2013.01); *G01N 33/18* (2013.01)
  USPC ............ 701/29.5; 701/32.8; 701/32.9; 703/2; 73/54.02
(58) Field of Classification Search
  USPC ................ 701/99, 101, 102, 29.1, 29.4, 29.5, 701/31.4, 32.8, 32.9; 703/2; 73/54.01, 73/54.02
  See application file for complete search history.

(56) References Cited

U.S. PATENT DOCUMENTS

| | | | |
|---|---|---|---|
| 6,497,212 B2 * | 12/2002 | Matsumoto et al. | .......... 123/295 |
| 6,553,812 B2 | 4/2003 | Park | |
| 6,681,172 B2 | 1/2004 | Pfeiffer | |
| 6,732,572 B1 * | 5/2004 | Pickert et al. | ................. 73/54.01 |
| 6,742,498 B2 * | 6/2004 | Mabuchi et al. | ............. 123/339.16 |
| 7,347,168 B2 * | 3/2008 | Reckels et al. | ............. 123/41.11 |
| 7,424,868 B2 * | 9/2008 | Reckels et al. | ............... 123/41.1 |
| 7,677,086 B2 | 3/2010 | Albertson et al. | |
| 8,019,568 B2 | 9/2011 | Lehner | |
| 2008/0149407 A1 * | 6/2008 | Shibata et al. | ............... 180/65.2 |
| 2009/0192728 A1 * | 7/2009 | Wright et al. | ................... 702/33 |
| 2010/0101519 A1 | 4/2010 | Carrick | |

OTHER PUBLICATIONS

Wakuri, et al., Studies on Friction Characteristics of Reciprocating Engines, SAE Technical Paper Series, 1995, pp. 41-55, Society of Automotive Engineers, Inc.

Choi, et al, A Study of the Friction Characteristics of Engine Bearing and Cam/Tappet Contacts from the Measurement of Temperature and Oil Film Thickness, SAE Technical Paper Series, 1995, pp. 58-66, Society of Automotive Engineers, Inc.

(Continued)

*Primary Examiner* — Russell Frejd (57) ABSTRACT

A powertrain control module determines engine oil properties based on friction in an engine. The powertrain control module includes an engine combustion module that models engine torque based on engine speed and engine pumping losses due to intake and exhaust gasses. A transmission module models transmission torque applied to the engine based on transmission speed and gear. An accessory loads module models torque applied to the engine by accessory loads including at least one of a power steering pump, an air conditioning compressor, a water pump, and an alternator. An oil viscosity module determines engine oil viscosity based on a friction torque and predetermined engine data that coincides with reference oils. The friction torque is based on the engine torque, transmission torque, and accessory loads torque.

20 Claims, 5 Drawing Sheets

(56) References Cited

OTHER PUBLICATIONS

Agoston, A et al. Viscosity Sensors for Engine Oil Condition Monitoring—Application and Interpretation of Results, Sensors and Actuators A, 2005, pp. 327-332, vol. 121, Elsevier.

Skjoedt, et al., Effects of Oil Properties on Spark-Ignition Gasoline Engine Friction, Tibology International, 2008, pp. 556-563, vol. 41, Elsevier.

Han, et al., Engine Oil Viscometer Based on Oil Pressure Sensor, Delphi Research Labs, 2006.

* cited by examiner

ENGINE FRICTION BASED OIL VISCOSITY MONITOR

FIELD

The present disclosure relates to real-time determination of engine oil viscosity in an internal combustion engine.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Some modern vehicles employ variable valve timing or other hydraulic systems. In some implementations the responsiveness of those systems are limited by the engine oil viscosity. Predicting the behavior of those systems becomes complicated when it is appreciated that engine oil viscosity changes as the oil ages and components are broken down. Engine oil viscosity also changes based on oil temperature. While there are sensors available that can help determine engine oil viscosity in real time there remains a need in the art for alternate solutions.

SUMMARY

A powertrain control module determines engine oil properties based on friction in an engine. The powertrain control module includes an engine combustion module that models engine torque based on engine speed and engine pumping losses due to intake and exhaust gasses. A transmission module models transmission torque applied to the engine based on transmission speed and gear. An accessory loads module models torque applied to the engine by accessory loads including at least one of a power steering pump, an air conditioning compressor, a water pump, and an alternator. An oil viscosity module determines engine oil viscosity based on a friction torque and predetermined engine data that coincides with reference oils. The friction torque is based on the engine torque, transmission torque, and accessory loads torque.

In other features an oil classification module determines an SAE oil grade based on the engine oil viscosity. A viscosity temperature coefficient module determines at least one of a viscosity index and a viscosity temperature coefficient based on the estimated viscosity and an engine oil temperature.

In other features the oil viscosity module includes first and second lookup tables that represent expected friction torques with reference engine oils of a first viscosity and a second viscosity, respectively, at a given engine speed and oil temperature. The oil viscosity module further includes third and fourth lookup tables that represent viscosities of the reference engine oils of the first viscosity and the second viscosity, respectively, at a given engine speed and oil temperature. The oil viscosity module determines a viscosity interpolation factor based on the friction torque and the expected friction torques and calculates the estimated viscosity based on the viscosity interpolation factor and the viscosities of the reference engine oils of the first viscosity and the second viscosity, respectively, at a given engine speed and oil temperature.

A method of determining engine oil properties based on friction in an engine is described. The method includes modeling engine torque based on engine speed and engine pumping losses due to intake and exhaust gasses, modeling transmission torque applied to the engine based on transmission speed and gear, modeling torque applied to the engine by accessory loads including at least one of a power steering pump, an air conditioning compressor, a water pump, and an alternator determining engine oil viscosity based on a friction torque and predetermined engine data that coincides with reference oils, and determining friction torque based on the engine torque, transmission torque, and accessory loads torque.

In other features the method determines an SAE oil grade based on the engine oil viscosity. The method can also determine at least one of a viscosity index and a viscosity temperature coefficient based on the estimated viscosity and an engine oil temperature.

In other features the method includes looking up first and second expected friction torques with reference engine oils of a first viscosity and a second viscosity, respectively, at a given engine speed and oil temperature. The method can also include generating looking up viscosities of the reference engine oils of the first viscosity and the second viscosity, respectively, at a given engine speed and oil temperature. The method can also include determining a viscosity interpolation factor based on the friction torque and the expected friction torques and calculating the estimated viscosity based on the viscosity interpolation factor and the viscosities of the reference engine oils of the first viscosity and the second viscosity, respectively, at a given engine speed and oil temperature.

A powertrain control module determines engine oil properties based on friction in an engine. The powertrain control module includes engine combustion means for modeling engine torque based on engine speed and engine pumping losses due to intake and exhaust gasses, transmission means for modeling transmission torque applied to the engine based on transmission speed and gear, accessory loads means for modeling torque applied to the engine by accessory loads including at least one of a power steering pump means for power steering, air conditioning compressor means for air conditioning, water pump means for pumping coolant, and alternator means for charging a battery; and oil viscosity means for determining engine oil viscosity based on a friction torque and predetermined engine data that coincides with reference oils and wherein the friction torque is based on the engine torque, transmission torque, and accessory loads torque.

In other features the powertrain control module further includes oil classification means for determining an SAE oil grade based on the engine oil viscosity. The powertrain control module can also include a viscosity temperature coefficient means for determining at least one of a viscosity index and a viscosity temperature coefficient based on the estimated viscosity and an engine oil temperature.

In other features the oil viscosity means further comprises first and second lookup tables that represent expected friction torques with reference engine oils of a first viscosity and a second viscosity, respectively, at a given engine speed and oil temperature. The oil viscosity means further includes third and fourth lookup tables that represent viscosities of the reference engine oils of the first viscosity and the second viscosity, respectively, at a given engine speed and oil temperature. The oil viscosity means determines a viscosity interpolation factor based on the friction torque and the expected friction torques and calculates the estimated viscosity based on the viscosity interpolation factor and the viscosities of the reference engine oils of the first viscosity and the second viscosity, respectively, at a given engine speed and oil temperature.

A method of determining engine oil properties based on friction in an engine is implemented by a computer program executed by one or more processors. The computer program can reside on a computer readable medium such as but not limited to memory, non-volatile data storage and/or other suitable tangible storage mediums. The computer program includes modeling engine torque based on engine speed and engine pumping losses due to intake and exhaust gasses, modeling transmission torque applied to the engine based on transmission speed and gear, modeling torque applied to the engine by accessory loads including at least one of a power steering pump, an air conditioning compressor, a water pump, and an alternator determining engine oil viscosity based on a friction torque and predetermined engine data that coincides with reference oils, and determining friction torque based on the engine torque, transmission torque, and accessory loads torque.

In other features the computer program determines an SAE oil grade based on the engine oil viscosity. The computer program can also determine at least one of a viscosity index and a viscosity temperature coefficient based on the estimated viscosity and an engine oil temperature.

In other features the computer program includes looking up first and second expected friction torques with reference engine oils of a first viscosity and a second viscosity, respectively, at a given engine speed and oil temperature. The computer program can also include generating looking up viscosities of the reference engine oils of the first viscosity and the second viscosity, respectively, at a given engine speed and oil temperature. The computer program can also include determining a viscosity interpolation factor based on the friction torque and the expected friction torques and calculating the estimated viscosity based on the viscosity interpolation factor and the viscosities of the reference engine oils of the first viscosity and the second viscosity, respectively, at a given engine speed and oil temperature.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module refers to an Application Specific Integrated Circuit (ASIC), an electronic circuit, a processor (shared, dedicated, or group) and memory that execute one or more software or firmware programs, a combinational logic circuit, and/or other suitable components that provide the described functionality.

Figure 1:
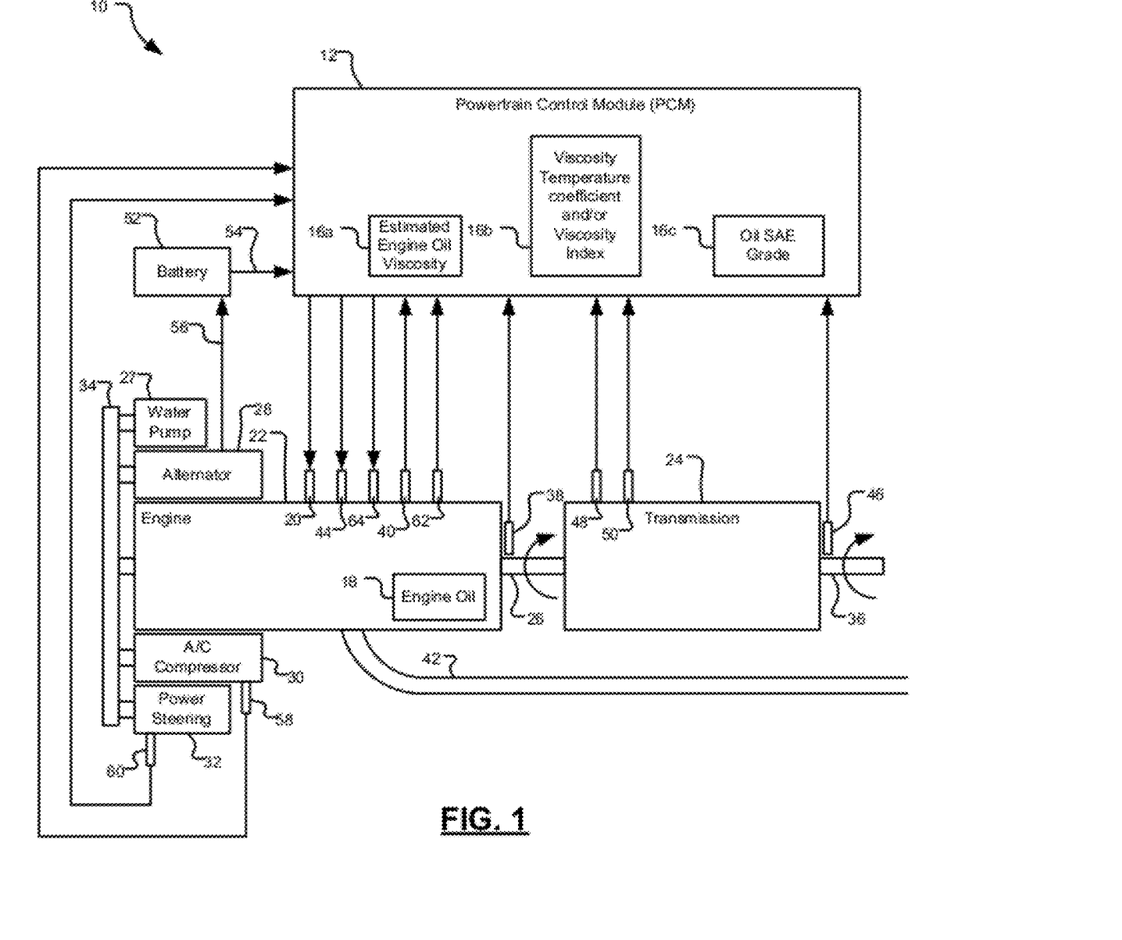
FIG. 1 is a functional block diagram of a powertrain control system that estimates engine oil viscosity.

Referring now to FIG. 1, a functional block diagram is shown of a powertrain control system 10. Powertrain control system 10 includes a powertrain control module (PCM) 12. PCM 12 executes an algorithm 14 (shown in FIG. 2) that generates and stores an estimated engine oil viscosity 16a, a viscosity index (and/or viscosity temperature coefficient) 16b, and an oil SAE grade 16c. Estimated engine oil viscosity 16a represents the viscosity of an engine oil 18. Estimated engine oil viscosity 16a is used to model and/or anticipate system response of an oil dependent actuator 20. Examples of oil dependent actuator 20 include variable valve timing or other such systems whose motion is dependent on the viscosity of engine oil 18.

The basic elements of powertrain control system 10 will now be described. The elements are familiar to those skilled in the art and perform their normal functions as is known in the art. An engine 22 produces torque for driving a transmission 24. A rotating transmission input shaft 26 connects engine 22 and transmission 25. Engine 22 also produces torque for driving accessory loads such as a water pump 27, an alternator 28, an air conditioning compressor 30, and a power steering pump 32. An accessory drive 34 provides engine torque to the accessory loads. A transmission output shaft 36 provides driving torque to drive wheels via a traditional axle and differential assembly (not shown).

The operation of PCM 12 will now be described in more detail. PCM 16 generates estimated engine oil viscosity 16a and index (and/or viscosity temperature coefficient) 16b based on inputs from several sensors and/or modeled engine parameters. An engine speed sensor 38 generates a signal based on the rotational speed of engine 22. An intake manifold pressure sensor 40 generates a signal based on air pressure in an intake manifold of engine 22. PCM 12 estimates exhaust manifold pressure 42 based on empirical data. PCM 12 provides calculated spark timing 44 that determines an ignition angle of engine 22. A transmission output speed sensor 46 generates a signal based on a rotational speed of transmission output shaft 36. A transmission gear sensor 48 generates a signal based on a gear ratio of transmission 24. In a vehicle with a manual transmission 24 a clutch pedal upstop switch 50 generates signal based on a clutch pedal position.

A battery 52 provides battery voltage 54 to PCM 12. Battery 52 is charged by charging current 56 from alternator 28. An air conditioning pressure sensor 58 generates a signal based on refrigerant pressure. A power steering pressure sensor 60 generates a signal based on power steering fluid pressure. An oil temperature sensor 62 generates a signal based on the temperature of engine oil 18. An idle speed actuator 64 controls an idle speed of engine 22 based on a command signal from PCM 12 which controls the air flow to the engine.

Figure 2:
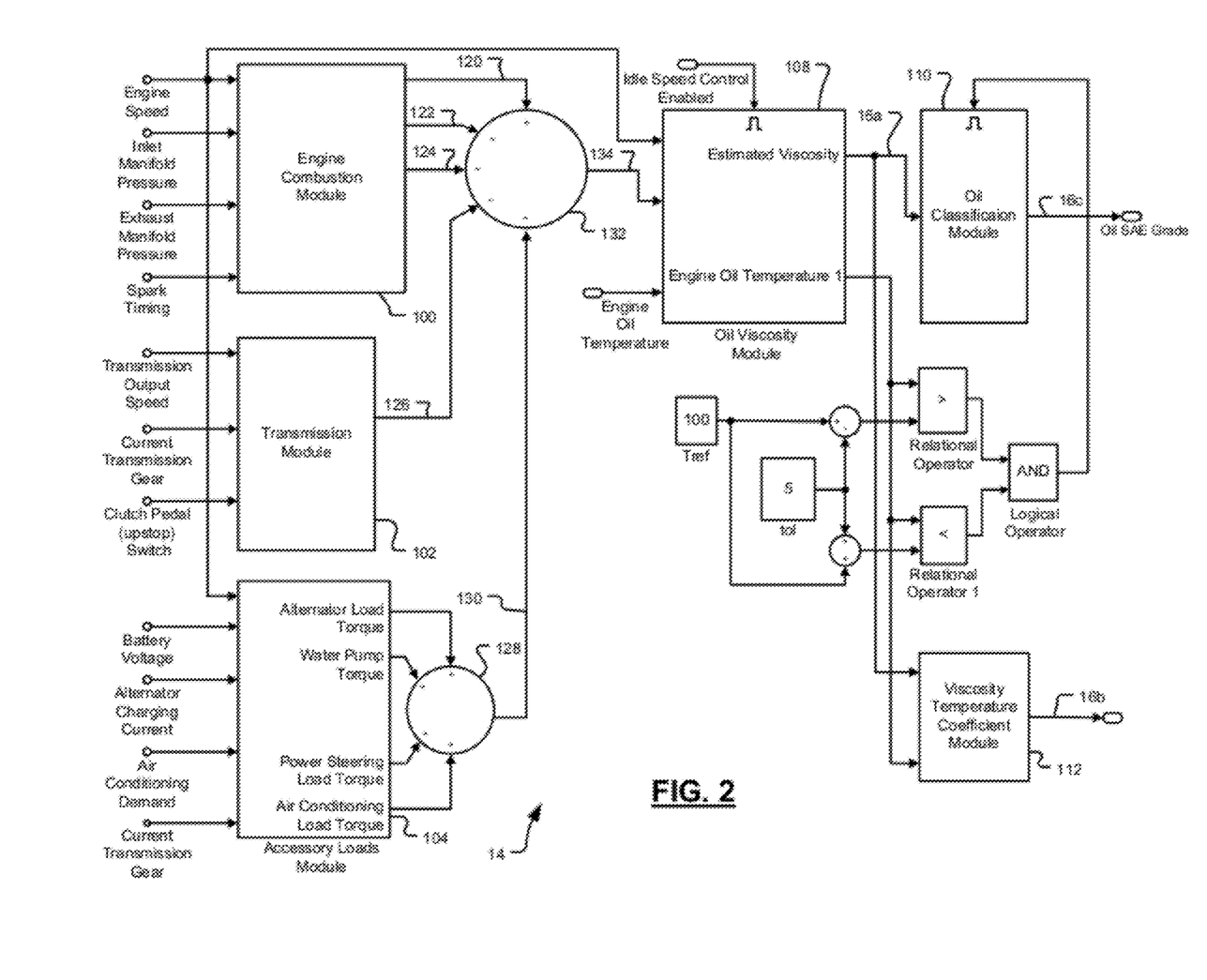
FIG. 2 is a functional block diagram of an engine oil viscosity estimation algorithm.

Referring now to FIG. 2, a block diagram is shown of algorithm 14. Algorithm 14 generates 16a and 16b based on friction torque in engine 22. In some embodiments algorithm 14 executes in its entirety only when engine 22 is at idle and transmission 24 is in park and/or neutral.

An engine combustion module 100 estimates the amount of torque produced and consumed by engine 22. The estimation is based on empirical data and/or engine modeling as is known in the art. The input data includes engine speed that is based on the signal from engine speed sensor 38, inlet manifold pressure that is based on the signal from manifold pressure sensor 40, estimated exhaust manifold pressure 42, and calculated spark timing 44. An indicated combustion torque 120 represents the amount of torque produced by engine 22. A pumping torque 122 represents the amount of torque consumed by pumping losses in engine 22. An engine acceleration torque 124 represents the amount of torque consumed by engine 22 as its moving mass is accelerated.

A transmission module 102 estimates the amount of torque that transmission input shaft 26 applies to engine 22. The estimation is based on empirical data and/or transmission modeling as is known in the art. The input data includes transmission output speed based on the signal from transmission output speed sensor 46, current transmission gear based on the signal from transmission gear sensor 48, and, if transmission 22 is manual, the signal from clutch pedal upstop switch 50. The output of transmission module 102 represents transmission/torque converter load torque 126.

An accessory loads module 104 estimates the amount of torque that accessory loads and alternator 28 apply to engine 22. The estimation is based on empirical data and/or accessory load modeling as is known in the art. The input data includes engine speed based on the signal from engine speed sensor 38, battery voltage 54, alternator charging current 56, air conditioning demand based on whether air conditioning compressor 30 is running and the signal from air conditioning pressure sensor 58, and power steering load based on the signal from power steering pressure sensor 60.

A first summation module 128 generates a total accessory load torque 128 based on the sum of alternator load torque, water pump torque, power steering load torque, and air conditioning load torque.

A second summation module 132 generates an estimated engine friction 134 based on the outputs of engine combustion module 100, transmission module 102, and accessory loads module 104. Second summation module 132 begins with indicated combustion torque and then subtracts pumping torque 122, engine acceleration torque 124, transmission/torque converter load torque 126 and total accessory load torque 130. The remainder is estimated engine friction 134. Algorithm 14 employs the estimated engine friction to estimate engine oil viscosity.

An oil viscosity module 108 generates estimated oil viscosity 16a based on the engine speed, estimated engine friction 134, engine oil temperature, and idle speed control that controls idle speed actuator 64. Oil viscosity module 108 is enabled when the engine oil temperature and estimated viscosity 16a falls within respective predetermined ranges for oil classification. Oil viscosity module 108 is explained in more detail below and shown in more detail in FIG. 3.

An oil classification module 110 generates SAE oil grade 16c based on estimated oil viscosity 16a at a given temperature. In the depicted embodiment the temperature is 100 deg C. +/−5 deg C. however it should be appreciated that a different temperature and/or tolerance range may be used depending available oil viscosity vs. SAE grade data. Oil classification module 110 is explained in more detail below and shown in more detail in FIGS. 4 and 5.

A viscosity temperature coefficient module 112 generates oil viscosity temperature coefficient 16c based on estimated viscosity 16a and engine oil temperature. Viscosity temperature coefficient module 112 is explained in more detail below and shown in more detail in FIG. 6.

Figure 3:
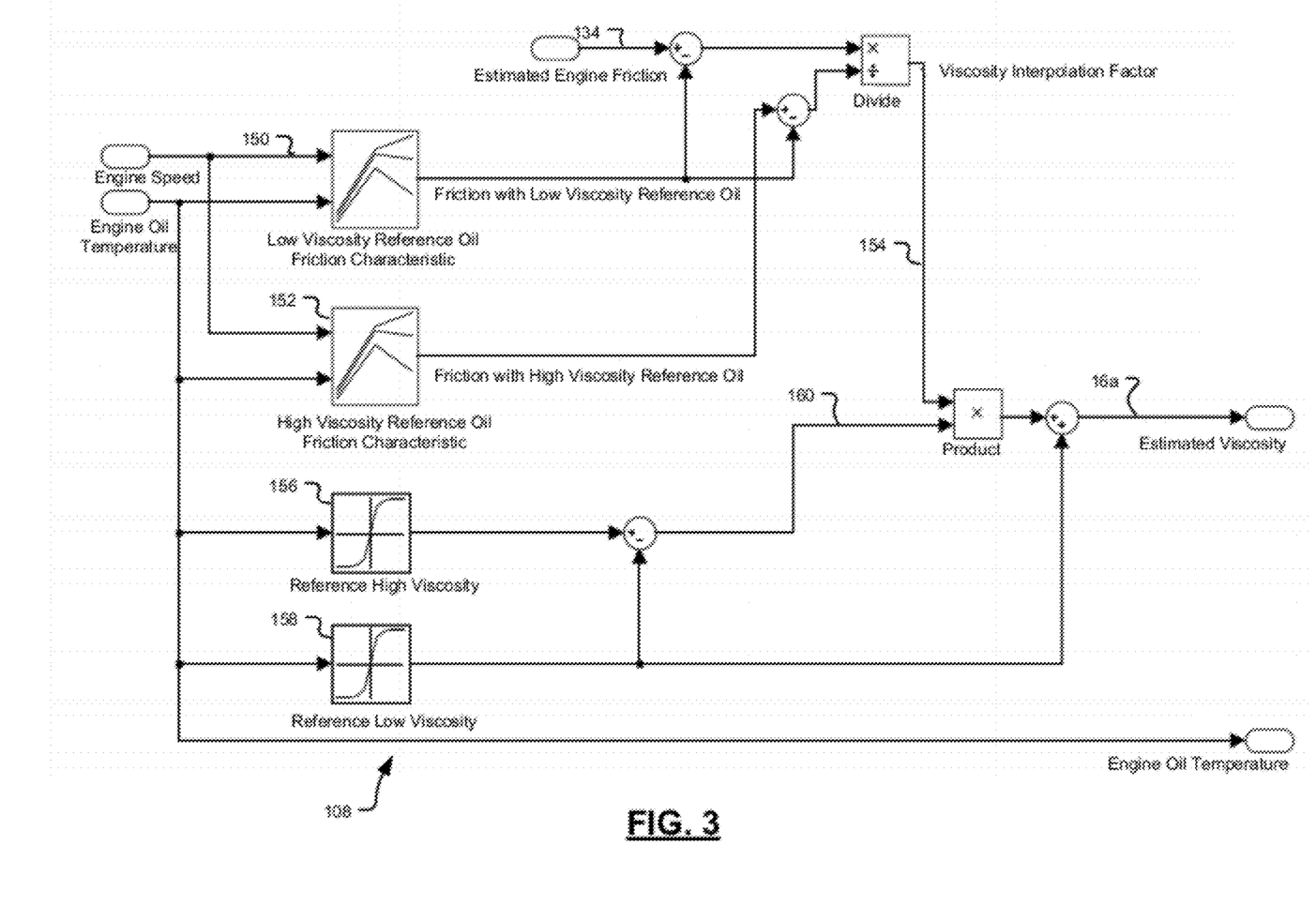
FIG. 3 is a functional block diagram of an oil viscosity monitor module.

Referring now to FIG. 3, a functional block diagram is shown of oil viscosity module 108. Oil viscosity module 108 includes four lookup tables that contain experimentally determined data. During operation the data is interpolated based on the engine speed, engine oil temperature, and estimated engine friction 134.

A first lookup table 150 characterizes the low viscosity reference oil friction of engine 22. The data of first lookup table 150 is obtained by directly or indirectly measuring the friction torque of engine 122 over predetermined ranges of engine speeds and engine oil temperatures with a low viscosity oil. In some embodiments the low viscosity oil is SAE 10W. In some embodiments the range of engine speeds is equal to an idle speed control range of idle speed actuator 64. In some embodiments the idle speed control range is 500-1500 RPM.

A second lookup table 152 characterizes the high viscosity reference oil friction of engine 22. The data of second lookup table 152 is obtained by directly or indirectly measuring the friction torque of engine 122 over the same predetermined ranges of engine speeds and engine oil temperatures as first lookup table 150. In some embodiments the high viscosity oil is SAE 50W.

A third lookup table 156 characterizes the viscosity of the high viscosity reference oil that was used in to gather the data in second lookup table 152. The characterization is done as a function of the same engine oil temperature range that was used to obtain the data in second lookup table 152.

A fourth lookup table 158 characterizes the viscosity of the low viscosity reference oil that was used in to gather the data in first lookup table 150. The characterization is done as a function of the same engine oil temperature range that was used to obtain the data in first lookup table 150.

During operation the engine speed and engine oil temperature are employed to look up the friction of engine 22. The friction with the low viscosity oil is obtained from first lookup table 150. The friction with the high viscosity oil is obtained from second lookup table 152. Estimated engine friction 134 is then used to determine a unitless viscosity interpolation factor 154 based on the frictions with the low and high viscosity oils.

Also during operation the engine oil temperature is employed to look up the viscosities of the high and low viscosity oils from third lookup table 156 and fourth lookup table 158, respectively. A viscosity difference 169 is then determined based on the results of those table lookups.

Estimated viscosity 16a is determined based on using viscosity interpolation factor 154 to interpolate between the results from third lookup table 156 and fourth lookup table 158.

Figure 4:
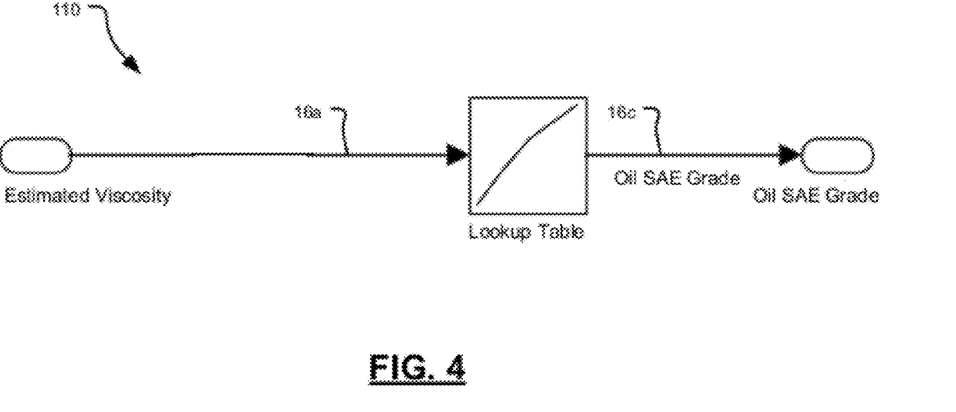
FIG. 4 is a functional block diagram of an oil classification module.
Figure 5:
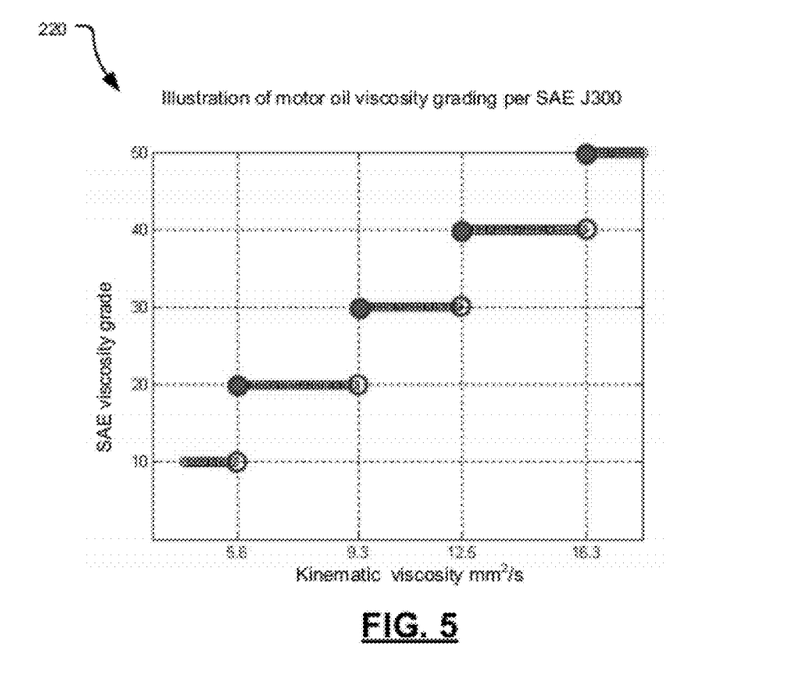
FIG. 5 is a graph of sample oil classification data that is employed by the oil classification function of FIG. 5.

Referring now to FIGS. 4 and 5 operation of oil classification module 110 will be described. Oil classification module 110 employs estimated viscosity 16a to classify engine oil 18 into one of several predetermined oil viscosity ranges. In some embodiments the viscosity ranges are defined by SAE publication J300 as is known in the art. The viscosity ranges are stored in a fifth lookup table 220. Estimated viscosity 16a is used to index into fifth lookup table 220. FIG. 5 depicts an embodiment of fifth lookup table 220 that implements the SAE J300 oil classifications at a specified temperature. In the depicted embodiment the specified temperature is noted as Tref in FIG. 2, for example 100 deg C. In a more general case, fifth lookup table 220 can be expanded to as a 2D function of viscosity and temperature.

Figure 6:
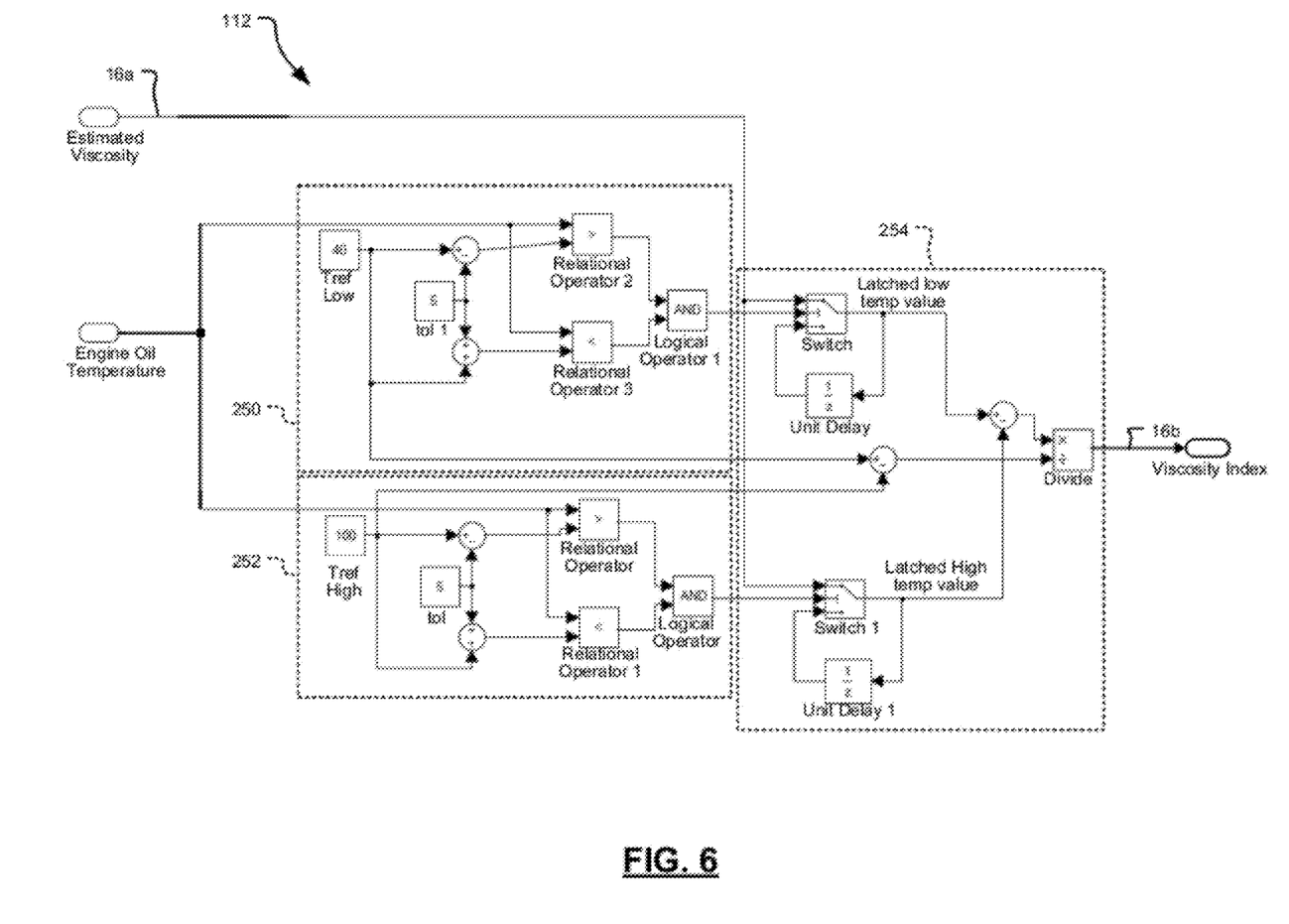
FIG. 6 is a functional block diagram of a viscosity temperature coefficient module.

Referring now to FIG. 6, a functional block diagram is shown of viscosity temperature coefficient module 112. It determines index (and/or viscosity temperature coefficient) 16b based on the engine oil temperature and estimated viscosity 16a. Viscosity index is an important characteristic of multi-grade oils and one of the most prone to deterioration or aging as index improvers in the oil and the oil molecules themselves break down. By SAE standard the reference temperatures for viscosity index are 40 deg C. and 100 deg C. The viscosity index of the oil is calculated and monitored by comparing the learned viscosity 16a in cells 200 defined around 40 deg C. oil temperature with the learned viscosity in cells 200 defined around 100 deg C. oil temperature. For example if engine oil 18 is originally 10W30 and the 40 deg C. cell has classified engine oil 18 as an SAE 30 then the oil's index improvers have broken down. The viscosity index 16b can be calculated according to the formula $$vi = [(l-h)/(L-H)] \ast 100 \quad \text{(Eq. 1)}$$

where vi is viscosity index 16b, l is estimated viscosity 16a at a predetermined low oil temperature, h is estimated viscosity 16a at a predetermined high oil temperature, L is the predetermined low oil temperature, and H is the predetermined high oil temperature. In some embodiments L and H are 40 deg C. and 100 deg C., respectively.

A low temperature enable module 250 outputs a true signal when the engine oil temperature reaches the predetermined low oil temperature plus a tolerance band. In the depicted embodiment the predetermined low oil temperature is 40 deg C. and the tolerance band is +/−5 deg C.

A high temperature enable module 252 outputs a true signal when the engine oil temperature reaches the predetermined high oil temperature plus a tolerance band. In the depicted embodiment the predetermined high oil temperature is 100 deg C. and the tolerance band is +/−5 deg C.

A calculation module 254 executes Eq. 1 when it receives the true signals from low and high temperature enable modules 250 and 252.

In addition to or instead of calculating the viscosity index 16b, viscosity temperature coefficient module 112 can calculate a viscosity temperature coefficient. The viscosity temperature coefficient is a parameter for the rate of change of the logarithm of oil viscosity vs. oil temperature. It is calculated in a similar manner to FIG. 6 except the latched values at the high and low temperatures are the logarithm of the estimated viscosity 16a. The viscosity temperature coefficient can be used over any expected range for high and low oil temperatures. Whereas the viscosity index can only be calculated at the predefined temperatures of 40 C and 100 C for purposes of comparison. Multi-rage oils with index improvers (low viscosity index) will have a smaller (less negative) viscosity temperature coefficient.

PCM 12 controls oil dependent actuator 20 (shown in FIG. 1) based at least one of estimated oil viscosity 16a, viscosity index and/or viscosity temperature coefficient 16b, and SAE oil classification 16c.

Those skilled in the art can now appreciate from the foregoing description that the broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A powertrain control module that determines engine oil properties based on friction in an engine, comprising:
   an engine combustion module that models engine torque based on a signal indicative of engine speed from an engine speed sensor and a signal indicative of engine pumping losses due to intake and exhaust gasses from at least one pressure sensor,
   a transmission module that models transmission torque applied to the engine based on a signal indicative of transmission speed from a transmission speed sensor and a signal indicative of a current gear, from a gear sensor,
   an accessory loads module that models torque applied to the engine by accessory loads based on received signals from at least one accessory sensor indicative of the operation of at least one of a power steering pump, an air conditioning compressor, a water pump, and an alternator; and
   an oil viscosity module that determines engine oil viscosity based on a signal indicative of friction torque and predetermined engine data that coincides with reference oils and wherein the friction torque is based on the model of engine torque, the model of transmission torque, and the model of accessory loads torque, wherein the determined oil viscosity is utilized to modify operation of at least one engine operating characteristic.

2. The powertrain control module of claim 1 further comprising an oil classification module that determines an SAE oil grade based on the engine oil viscosity.

3. The powertrain control module of claim 1 further comprising a viscosity temperature coefficient module that determines at least one of a viscosity index and a viscosity temperature coefficient based on the estimated viscosity and an engine oil temperature.

4. The powertrain control module of claim 1 wherein the oil viscosity module further comprises first and second lookup tables that represent expected friction torques with reference engine oils of a first viscosity and a second viscosity, respectively, at a given engine speed and oil temperature.

5. The powertrain control module of claim 4 wherein the oil viscosity module further comprises third and fourth lookup tables that represent viscosities of the reference engine oils of the first viscosity and the second viscosity, respectively, at a given engine speed and oil temperature.

6. The powertrain control module of claim 5, wherein the oil viscosity module determines a viscosity interpolation factor based on the friction torque and the expected friction torques and calculates the estimated viscosity based on the viscosity interpolation factor and the viscosities of the reference engine oils of the first viscosity and the second viscosity, respectively, at a given engine speed and oil temperature.

7. A method of determining engine oil properties based on friction in an engine, comprising:
   detecting an engine speed with an engine speed sensor;
   modeling engine torque based on the detected engine speed and engine pumping losses due to intake and exhaust gasses,
   detecting a transmission speed with an output speed sensor;
   detecting a current gear of the transmission with a gear sensor;
   modeling transmission torque applied to the engine based on the detected transmission speed from the output speed sensor and the detected gear from the gear sensor, detecting an accessory load on the engine with at least one sensor, wherein the at least one sensor generates a signal indicative of the accessory load;

modeling torque applied to the engine based on the signal indicative of at least one accessory load, wherein the at least one accessory load is generated by at least one of a power steering pump, an air conditioning compressor, a water pump, and an alternator;

determining engine oil viscosity based on a friction torque determined based on sensed information indicative of current engine operating conditions and predetermined engine data that coincides with reference oils; and determining friction torque based on the modeled engine torque, modeled transmission torque, and modeled accessory loads torque.

8. The method of claim 7 further comprising determining an SAE oil grade based on the engine oil viscosity.

9. The method of claim 7 further comprising determining at least one of a viscosity index and a viscosity temperature coefficient based on the determined viscosity and an engine oil temperature.

10. The method of claim 7 further comprising looking up first and second expected friction torques with reference engine oils of a first viscosity and a second viscosity, respectively, at a given engine speed and oil temperature.

11. The method of claim 10 further comprising generating looking up viscosities of the reference engine oils of the first viscosity and the second viscosity, respectively, at a given engine speed and oil temperature.

12. The method of claim 11 further comprising determining a viscosity interpolation factor based on the friction torque and the expected friction torques and calculating of the reference engine oils of the first viscosity and the second viscosity, respectively, at a given engine speed and oil temperature.

13. A powertrain control module that determines engine oil properties based on friction in an engine, comprising:

an engine combustion module for modeling engine torque based on received signals indicative of engine speed and engine pumping losses due to intake and exhaust gasses, a transmission module for modeling transmission torque applied to the engine based on received signals indicative of transmission speed and gear, an accessory loads module for modeling torque applied to the engine by accessory loads based on received signals from sensors detecting an operating characteristic from at least one of a power steering pump for power steering, air conditioning compressor for air conditioning, water pump for pumping coolant, and alternator for charging a battery; and an oil viscosity module for determining engine oil viscosity based on a friction torque and predetermined engine data that coincides with reference oils and wherein the friction torque is based on a model of the engine torque generated by the engine combustion module, a model of transmission torque generated by the transmission module, and a model of accessory loads torque generated by the accessory load module.

14. The powertrain control module of claim 13 further comprising an oil classification module for determining an SAE oil grade based on the determined engine oil viscosity.

15. The powertrain control module of claim 13 further comprising a viscosity temperature coefficient module for determining at least one of a viscosity index and a viscosity temperature coefficient based on the determined viscosity and a signal indicative of engine oil temperature from engine oil temperature sensor.

16. The powertrain control module of claim 13 wherein the oil viscosity module further comprises first and second lookup tables that represent expected friction torques with reference engine oils of a first viscosity and a second viscosity, respectively, at a given engine speed and oil temperature.

17. The powertrain control module of claim 16 wherein the oil viscosity module further comprises third and fourth lookup tables that represent viscosities of the reference engine oils of the first viscosity and the second viscosity, respectively, at a given engine speed and oil temperature.

18. The powertrain control module of claim 17 wherein the oil viscosity module determines a viscosity interpolation factor based on the friction torque and the expected friction torques and calculates the estimated viscosity based on the viscosity interpolation factor and the viscosities of the reference engine oils of the first viscosity and the second viscosity, respectively, at a detected engine speed and oil temperature.

19. The powertrain control module of claim 1, wherein the engine includes an oil dependent actuator, wherein operation of the oil dependent actuator is modified based on the determined engine oil viscosity.

20. The method of claim 7, including controlling operation of an oil dependent actuator based on the determined engine oil viscosity.

* * * * *